United States Patent [19]

Birkhahn et al.

[11] Patent Number: 5,693,850
[45] Date of Patent: Dec. 2, 1997

[54] NUTRITIVE WATER SOLUBLE GLYCEROL ESTERS OF HYDROXY BUTYRIC ACID

[75] Inventors: Ronald H. Birkhahn, Toledo, Ohio; Robert J. Clemens, Kingsport; Charles A. McCombs, Johnson City, both of Tenn.

[73] Assignee: Eastman Chemical Company, Kingsport, Tenn.

[21] Appl. No.: 470,399

[22] Filed: Jun. 6, 1995

Related U.S. Application Data

[62] Division of Ser. No. 129,281, Sep. 30, 1993, abandoned.

[51] Int. Cl.$^6$ .................................................. C07C 69/66
[52] U.S. Cl. ............................................................... 560/189
[58] Field of Search ................................... 560/189, 181

[56] References Cited

U.S. PATENT DOCUMENTS

| | | |
|---|---|---|
| 4,665,057 | 5/1987 | Nelson et al. . |
| 4,701,443 | 10/1987 | Nelson et al. . |
| 4,997,976 | 3/1991 | Brunengraber . |
| 5,093,044 | 3/1992 | Wretlind et al. . |

FOREIGN PATENT DOCUMENTS

| | | |
|---|---|---|
| 0318357 | 5/1989 | European Pat. Off. . |
| 0366631 | 5/1990 | European Pat. Off. . |
| 0348664 | 10/1990 | European Pat. Off. . |
| 2046091 | 11/1980 | United Kingdom . |
| WO90/02548 | 3/1990 | WIPO . |

OTHER PUBLICATIONS

R. H. Birkhahn et al, J. Nutrition, 109, 1168 (1979).
S. A. Kripke et al, J. of Surgical Research, 44, 436 (1988).
R. H. Birkhahn et al, J. of Surgical Research 47, 427 (1989).
S. Tanaka, J. of the Osaka City Medical center, 38, 781 (1989).
T. Nishihata et al., Chem. Pharm. Bull., 32, 2025 (1984).
T. Nishihata et al., Chem. Pharm. Bull., 72, 280 (1983).
Patent Abstracts of Japan, vol. 15, No. 256 (C–0845) 28 Jun. 1991 & JP,A,03 083 950 (Kanegafuchi Chem Ind Co Ltd) 9 Apr. 1991 (See Abstract).
Rylander, "Hydrogenation Methods," Academic Press, London (1985), pp. 66–77.

*Primary Examiner*—Gary Geist
*Assistant Examiner*—Jean F. Vollano
*Attorney, Agent, or Firm*—Mark A. Montgomery; Harry J. Gwinnell

[57] ABSTRACT

A process for the production of water soluble glycerol esters useful as parenteral nutrients is disclosed. The process comprises the reaction of glycerol or a protected glycerol and an acetoacetate ester or acetoacetate precursor, yielding an acetoacetyl glycerol which is thereafter reduced, providing a glycerol ester of 3-hydroxybutyric acid.

5 Claims, 4 Drawing Sheets

NUTRITIVE WATER SOLUBLE GLYCEROL ESTERS OF HYDROXY BUTYRIC ACID

This is a divisional application of application Ser. No. 08/129, 281, filed Sep. 30, 1993, now abandoned.

The present invention relates to nutritional compounds, more particularly glyceryl esters of hydroxy butyric acid as parenteral nutrients.

BACKGROUND

Parenteral nutrients are administered in peripheral or central veins to supplement a patient's diet. Total parenteral nutrition is a recent advance in the maintenance of patients having an impaired gastrointestinal capacity. Such patients may have lost the use of a large portion of their intestinal tract either permanently or due to surgical intervention as may be required in cancer or Crohn's disease, or temporarily as a result of chemotherapeutic drugs or in the treatment of diverticulitis. Total parenteral nutrition is utilized as an adjunct therapy for the critically ill patient who has a generally increased metabolic rate and is unable to eat. The intent of the nutritional support is to prevent the loss of body nitrogen and the resulting complications of multiple organ failure, infection and increased chances of morbidity and mortality.

The energy source most commonly used for intravenous feeding has been glucose because carbohydrates are important for oral diets. However, glucose has not been as effective as was originally anticipated, and more importantly, the route of administration bypasses the normal digestive regulatory mechanisms for controlling blood sugar. Thus, continued intravenous administration (i.v.) of glucose generally results in high blood glucose levels which may have adverse consequences to the patient (particularly diabetics). Additional problems which can arise from i.v. glucose administration include fatty liver, respiratory stress, immune function inhibition, increased insulin secretion and undesirable metabolic regulation. Furthermore, skeletal muscle tissue is not well protected from degradation upon glucose administration to patients with trauma.

Due to these complications, it has been impossible to intravenously administer all the nutritional needs of the human body. This shortcoming poses a formidable problem to clinicians who must attempt such parenteral support. The problem is not merely one of administering a correct amount of calories and nutrients, but rather deals with providing these nutrients in a form which will suppress the breakdown of body proteins (catabolism) such as muscle tissue. This problem extends to trauma patients, where the goal is to provide supplemental energy sources to meet the increased energetic demands of the healing process.

Attempts have been made to find substitutes for glucose that do not instill an insulin response and that do not break down the body proteins. Substrates with metabolic properties very similar to glucose but lacking a significant insulin response are the so-called ketone bodies, 3-hydroxybutyrate and acetoacetate. U.S. Pat. No. 5,093,044 discloses water insoluble glycerol esters containing two or three aceto acetyl groups or two or three hydroxy butyryl groups. These compounds are water insoluble and thus must be administered enterally or parenterally in emulsion form. Other glyceride esters disclosed in this patent are based on pyruvic acid and lactic acid. The following publications disclose the water soluble monoglyceride of acetoacetic acid that is metabolized in vivo. European Pat. Application 0348664 (1990); R. H. Birkhahn et al., J. Nutrition, 109, 1168 (1979); S. A. Kripke et al., J. of Surgical Research, 44, 436 (1988); R. H. Birkhahn et al., J. of Surgical Research, 47, 427 (1989); S. Tanaka, J. of the Osaka City Medical Center, 38, 781 (1989).

WO90/02548 discloses an energy substrate containing alpha-hydroxycarboxylic acid and glycerol ester.

U.S. Pat. No. 4,997,976 discloses the use of 1,3-butanediol acetoacetate in parenteral oral nutrition.

U.S. Pat. No. 4,665,057 discloses a variety of nutrient monoesters of saccharides and monoglycerides containing fatty acids of four to ten carbon atoms.

U.S. Pat. No. 4,701,443 discloses certain nutrient polyesters based on dibasic acids such as succinic acid which may also contain moieties such as sugars, acetoacetyl groups and 3-hydroxybutyryl groups.

In light of the above, it would be very desirable to be able to produce and use water soluble non-glucose based parenteral nutrients that are at least as effective as glucose in supporting body weight with less of an insulin response and less protein degradation.

SUMMARY OF THE INVENTION

The present invention relates to a parenteral nutrient composition that comprises at least one glycerol ester of 3-hydroxybutyric acid of the formula

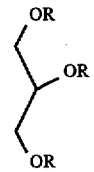

wherein each R is the same or different and is hydrogen, —(COCH$_2$CHOHCH$_3$) (A), or —(COCH$_2$COCH$_3$) (B), provided that at least one R is group (A).

The present invention also relates to a parenteral nutrient solution comprising a sterile aqueous solution of an effective amount of the above glycerol ester of 3-hydroxybutyric acid.

The present invention further relates to a process for the production of a glycerol ester of 3-hydroxybutyric acid that comprises:

(a) reacting at a temperature of about 0° to 180° C. glycerol or a protected glycerol and an acetoacetate ester, or acetoacetate precursor to produce an acetoacetyl glycerol wherein the protected glycerol is of the formula

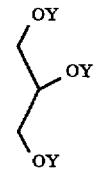

and wherein each Y group is either a protecting group or hydrogen with at least one Y group being hydrogen; and (b) reducing said acetoacetyl glycerol in the presence of hydrogen and a hydrogenation catalyst at a temperature of about 25° to 140° C.

(DL-1-(β-hydroxybutyryl)glycerol), glucose, or saline over a seven day period.

Figure 2:
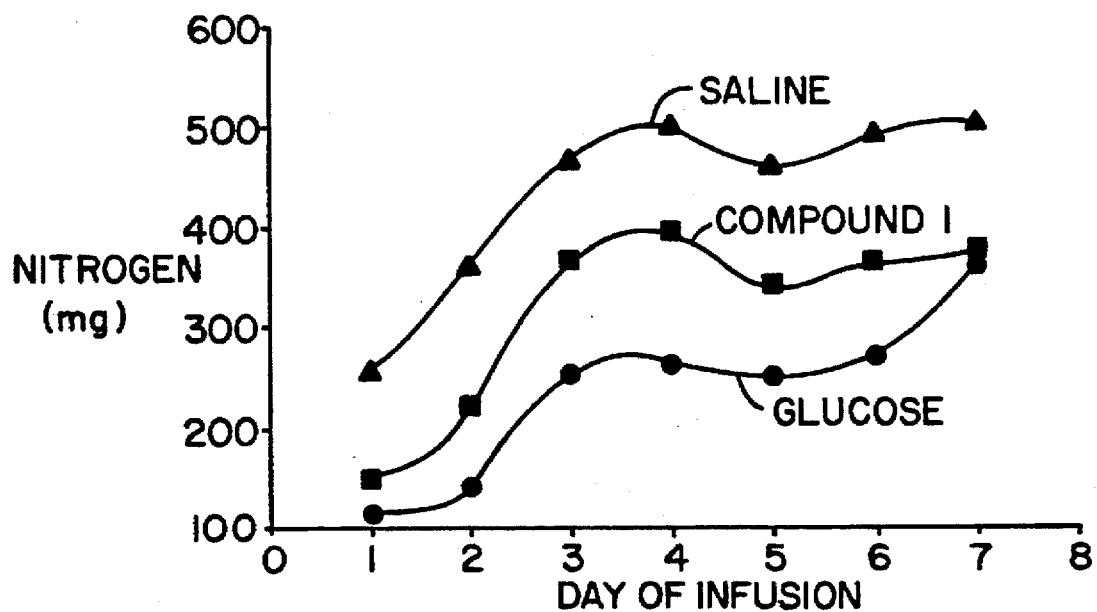

FIG. 2 shows the daily urinary nitrogen losses in milligrams for three groups of rats that were infused with Compound #1, glucose, or saline over a seven day period.

Figure 3:
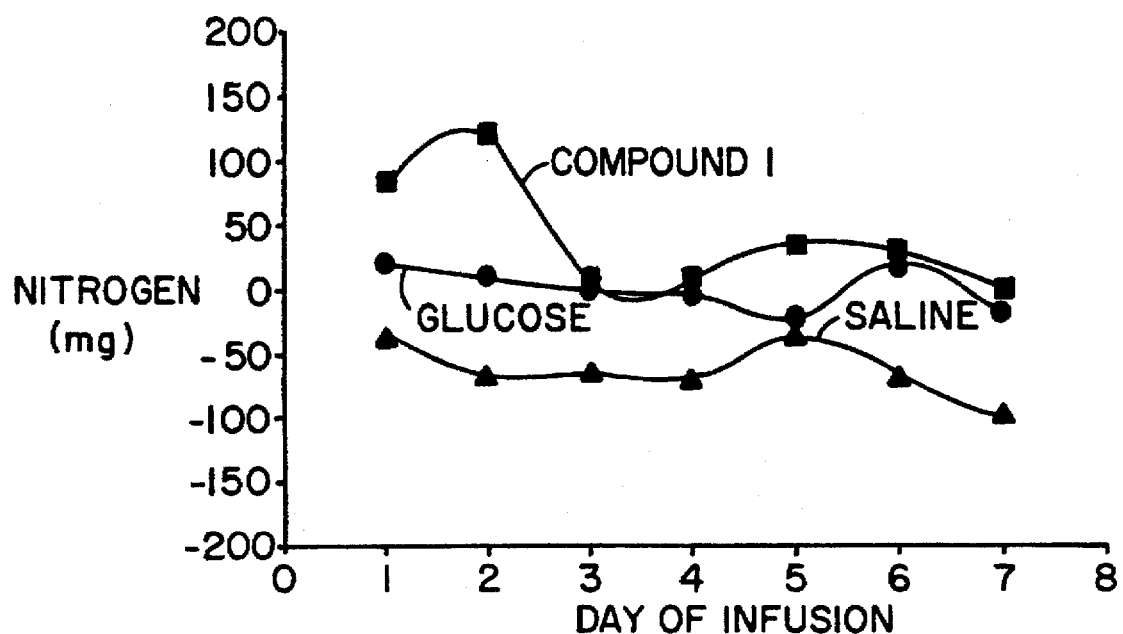

FIG. 3 shows the difference between dietary nitrogen intake and urinary nitrogen output in milligrams, which is nitrogen balance, for three groups of rats that were infused with Compound #1, glucose, or saline over a seven day period.

Figure 4:
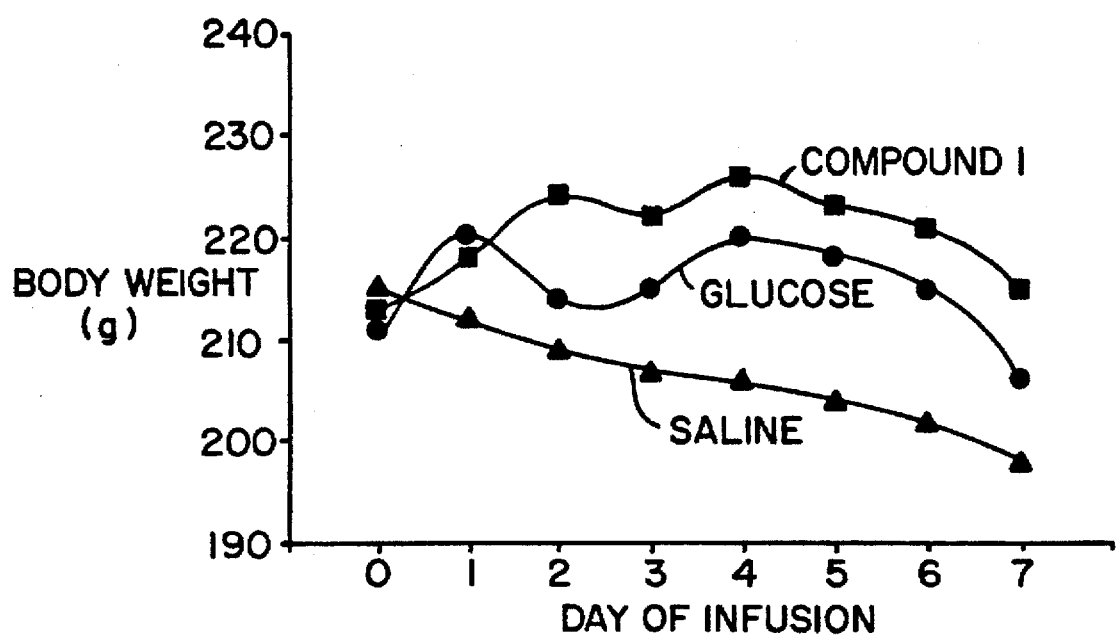

FIG. 4 shows the change in body weight in grams for three groups of rats that were infused with Compound #1, glucose, or saline over a seven day period.

Figure 5:
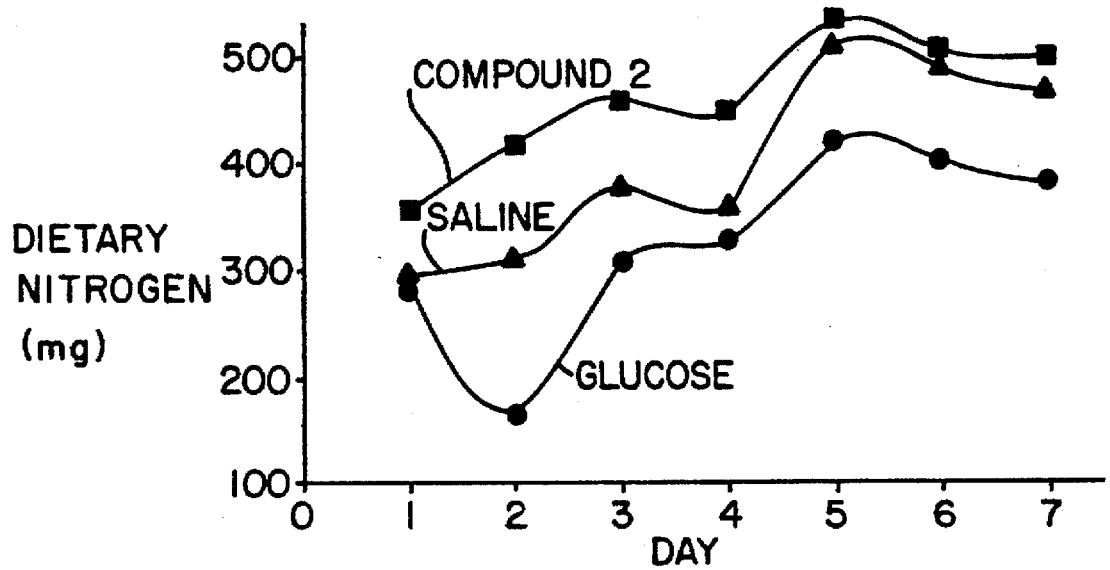

FIG. 5 shows the dietary nitrogen intake in milligrams for three groups of rats that were infused with Compound #2 (DL-tris-(β-hydroxybutyryl)glycerol), glucose, or saline over a seven day period.

Figure 6:
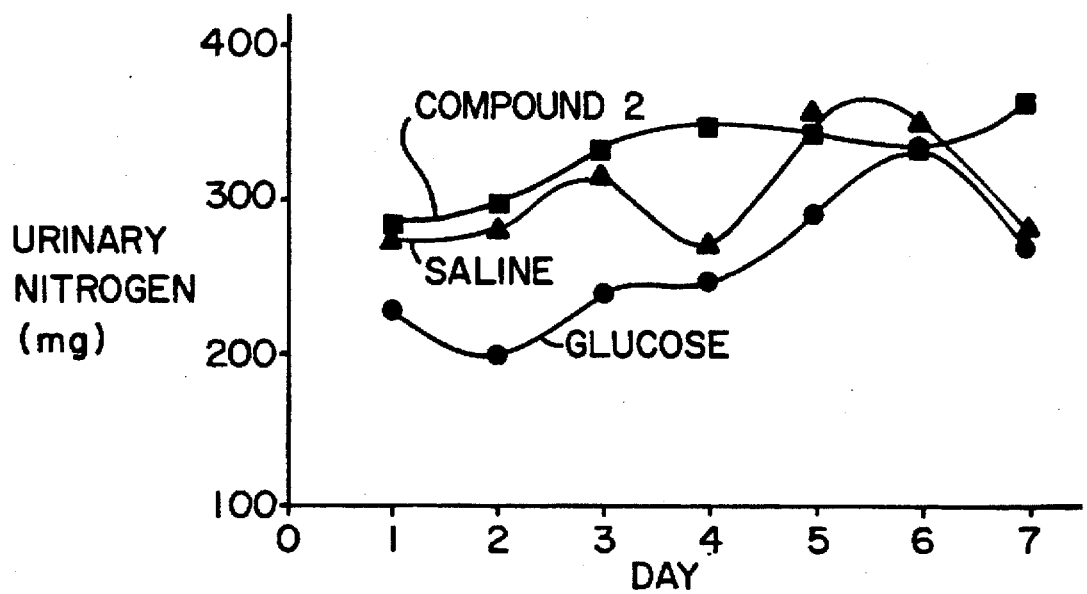

FIG. 6 shows the daily urinary nitrogen losses in milligrams for three groups of rats that were infused with Compound #2, glucose, or saline over a seven day period.

Figure 7:
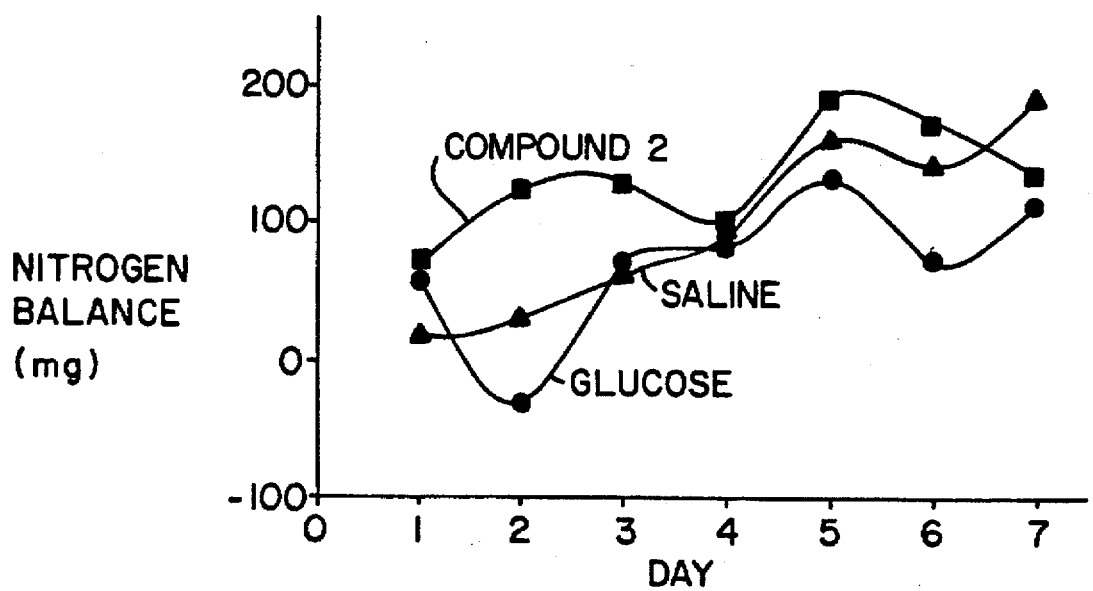

FIG. 7 shows the difference between dietary nitrogen intake and urinary nitrogen output in milligrams, which is nitrogen balance, for three groups of rats that were infused with Compound #2, glucose, or saline over a seven day period.

Figure 8:
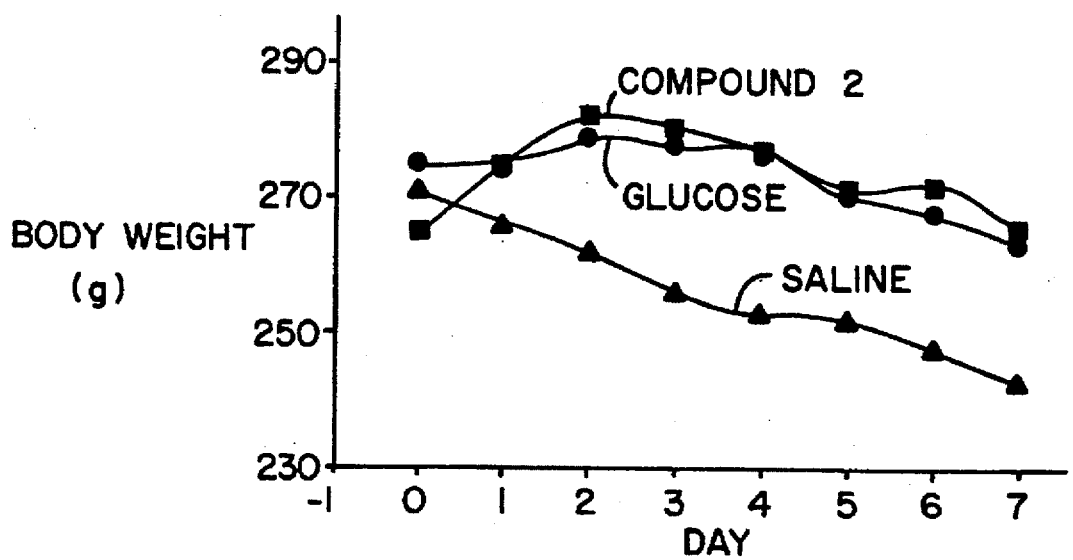

FIG. 8 shows the change in body weight in grams for three groups of rats that were infused with Compound #2, glucose, or saline over a seven day period.

DETAILED DESCRIPTION OF THE INVENTION

Applicants have unexpectedly discovered novel compounds that are nontoxic to mammals and are useful as parenteral nutrients. These novel compounds are water soluble and can be substituted for glucose, providing the energy requirement of the body receiving intravenous feeding without the complications caused by glucose infusion.

The novel compositions of the present invention preferably comprise glycerol esters of 3-hydroxybutyric acid of the formula

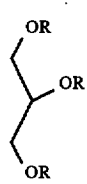

wherein each R is the same or different and is hydrogen or —(COCH$_2$CHOHCH$_3$)(A) provided that at least one R is not hydrogen.

When the glycerol ester of the present invention is multisubstituted (less than two R groups being hydrogen) it is preferred that these substituted R groups be completely reduced and all be group (A) or hydrogen. The completely reduced glycerol esters are more preferred due to ready water solubility. Specific examples of these glycerol esters of 3-hydroxybutyric acid include 1-(β-hydroxybutyryl) glycerol, bis(β-hydroxybutyryl) glycerol, and tris(β-hydroxybutyryl) glycerol with 1-(β-hydroxybutyryl) glycerol and tris(β-hydroxybutyryl) glycerol being most preferred due to ease in preparation.

The glycerol esters of 3-hydroxybutyric acid are preferably optically pure containing a majority of the composition in the form that is more readily metabolized by the body. This form is the D-β-(hydroxybutyryl) glycerol. When the inventive compound is 1-(β-hydroxybutyryl) glycerol, it is preferred that the isomer 1-(D-β-hydroxybutyryl) glycerol be in a concentration of at least 50%. When the inventive compound is tris(β-hydroxybutyryl) glycerol, it is preferred that the isomer tris(D-β-hydroxybutyryl) glycerol be in a concentration of at least 50%.

The novel compounds or compositions of the present invention are useful in a parenteral nutrient composition that comprises a sterile aqueous solution of an effective amount of at least one of the above glycerol esters of 3-hydroxybutyric acid.

These novel compounds or compositions are useful in stabilizing or increasing patient weight, reducing nitrogen loss and effecting other metabolic and physiological improvements in the clinical state of the patient. For parenteral administration, the selected compound or mixture of compounds is dissolved in an aqueous solution at the desired concentration. This concentration can be that which is intended for use, e.g., about 5 to 20 weight percent, or can be more concentrated, e.g. about 10 up to 50 weight percent or the saturation solubility limit of the compound. Concentrated solutions are maintained at the greater concentration to enhance the compound stability during autoclaving or storage. Such solutions then are diluted to the desired administration concentration at some convenient point before use. If necessary, the compound need not be dissolved in an aqueous solution at all until reconstitution before administration. This, however, is not as commercially desirable as supplying a ready-to-use solution.

The solution for administration frequently will be mixed with other nutrients or with drugs. Such other nutrients include nitrogen sources such as amino acids, essential fatty acids such as linoleic or linolenic acid, vitamins, minerals, and electrolytes including trace elements. Other calorie sources such as carbohydrates or lipids will not ordinarily be needed but can be supplied as required clinically. The amino acids are mixed with the compounds prior to or after sterilization. A mixture of essential amino acids nutritionally balanced will ordinarily be sufficient, although nonessential amino acids can be included. The proportions can be adjusted for special disease states, e.g., inborn errors of metabolism, in accord with known practice. Supplemental nutrients should also be selected to avoid adverse effects on the compounds during sterilization and/or storage. The pH can range about from 5.5 to 7.5. Other conventional additives such as antioxidants, buffers and the like can be included as well.

The solutions are packaged in conventional parenteral solution containers, either glass or thermoplastic flexible bags. Such containers are sterile sealed and contain means for connecting with the patient's circulation, either alone or in concert with other devices. Typically, the means for connecting with the patient's circulation will be a frangible member associated with the container which is adapted to enter into fluid connection with an administration set. Such sets also are well known.

The solutions usually are parenterally administered by infusion into a central or peripheral vein. The compound concentration is not critical. However, it should not be so low as to introduce undue amounts of water into the patient, nor so high as to cause peripheral vascular irritation. Generally an osmolarity below about 600 mOsm is satisfactory for peripheral parenteral infusion. Naturally, compounds containing the greatest number of calories per osmol are preferred. Less advantageously, the solution can be infused at a rate sufficient to maintain the nutritional status of the patient in concert with the intake of other nutrients. Infusion will be ordinarily about from 25 to 40 Kcal/Kg patient weight/day, but the amount administered parenterally will depend upon the patient's oral intake of the compounds or other nutrients.

Some of the compounds herein (particularly in the optically pure form) have the advantage of a higher energy content than glucose.

The process of producing the glycerol esters of 3-hydroxybutyric acid comprises (a) reacting at a temperature of about 0° to 180° C. glycerol or a protected glycerol and an acetoacetate ester or acetoacetate precursor to produce an acetoacetyl glycerol wherein the protected glycerol is of the formula

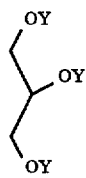

and wherein each Y group is either a protecting group or hydrogen with at least one Y group being hydrogen; and (b) reducing said acetoacetyl glycerol (glyceride) in the presence of hydrogen and a hydrogenation catalyst at a temperature of about 25° to 140° C.

When the starting glycerol reacted in Step (a) is a protected glycerol the resulting glycerol ester is not an entirely substituted glyceride (tris); and at least one of the remaining R groups is a protecting group. When a protecting group is present on the glycerol, this protecting group must be removed after the resulting glycerol ester composition is prepared, in order for the composition to be useful as a parenteral nutrient. Thus, the resulting product of Step (b) is further treated by hydrolyzing in the presence of an acid catalyst and an ion exchange resin at a temperature of about 0° to 60° C. to remove the protecting group.

Examples of suitable protecting groups include ketal and acetal protecting groups, commonly reacted with glycerol. To produce one of the preferred compounds of the present invention 2 Y's must be protecting groups. These 2 protecting groups can be the same compound such as a ketal with an acetonide being most preferred.

The acetoacetate ester reacted in Step (a) is preferably of the formula R'OCOCH$_2$COCH$_3$ wherein R' is aryl, alkyl or substituted alkyl. R' is preferably t-butyl, ethyl or methyl. Examples of suitable acetoacetate esters or acetoacetate precursors include tert-butylacetoacetate, methylacetoacetate, ethylacetoacetate, diketene, and 2,2,6-trimethyl-4H-1,3-dioxin-4-one (the diketene acetone adduct). For economic reasons diketene is the most preferred reagent for acetoacetylation of glycerol.

For liquid or molten glycerides, it is preferable that Step (b) be conducted in the absence of solvent. The absence of solvent greatly facilitates isolation of the product.

Step (b) in the process of the present invention is optionally conducted in an organic solvent. Specific examples of suitable organic solvents include ethyl acetate, butyl acetate, and mixtures thereof.

The process conducted in Step (b) is preferably conducted under a hydrogen pressure of about 200 to 10,000 psi, preferably about 200 to 1,000 psi with about 500 to 1,000 psi being most preferred. Hydrogen pressures much below 200 are not generally effective and require much longer reaction times and/or higher temperatures whereas pressures above 1,000 psi, and particularly above 10,000 psi, are generally more difficult to achieve.

The preferred hydrogenation catalyst used in Step (b) is a Raney nickel catalyst.

Specific preparatory schemes for the 2 most preferred compounds of the present invention are illustrated below.

Scheme 1

In making 1-(DL-β-hydroxybutyryl) glycerol (as shown below), solketal (2,2-dimethyl-1,3-dioxolane-4-methanol) is treated with diketene in the presence of basic catalysts such as tertiary amines at a temperature of about 0° C. to about 140° C. Suitable amines include trimethylamine, triethylamine, tripropylamine, pyridine, dimethylaminopyridine and the like. The intermediate solketal acetoacetate derivative is readily reduced using hydrogen and Raney nickel catalyst at a temperature of about 25° C. to about 140° C. Hydrogen pressures of about 200 psi to about 10,000 psi are generally used. This reduction is generally conducted in an organic solvent such as in ethyl acetate, butyl acetate and the like and provides a good yield of solketal-β-hydroxybutyrate[(2,2-dimethyl-1,3-dioxolan-4-yl) methyl 3-hydroxybutyrate]. The final stage of the process involves the acid catalyzed hydrolysis of the ketal at temperatures ranging from about 0° C. to about 60° C. A preferred acid catalyst is an acid ion exchange resin containing sulfonic acid groups.

In the first stage of the reaction, it is also possible to use tert-butyl acetoacetate instead of diketene to provide the desired acetoacetyl derivative. In this case, suitable reaction temperatures include about 70° C. to about 180° C.

SCHEME 1

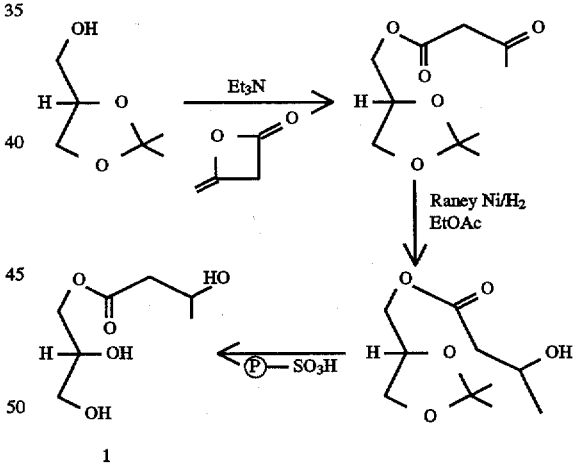

1

Scheme 2

In making DL-tris(β-hydroxybutyryl) glycerol according to Scheme 2 as shown below, glycerol is treated with tert-butyl acetoacetate at about 90° C. to about 180° C. in a suitable solvent. Alternatively, glycerol may be treated with diketene in the presence of a base catalyst. Suitable amine base catalysts include trimethylamine, triethylamine, tripropylamine, pyridine, dimethylaminopyridine and the like. The thusly produced trisacetoacetyl glycerol (1,2,3-propanetriyl acetoacetate) is readily reduced using hydrogen (200 psi to about 10,000 psi) in the presence of Raney nickel catalyst at a temperature in the range of about 25° C. to about 140° C. Suitable solvents include ethyl acetate, butyl acetate and the like.

SCHEME 2

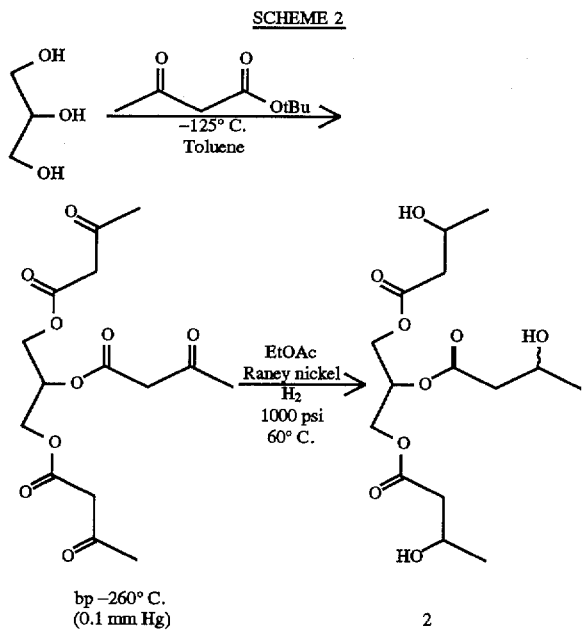

bp -260° C.
(0.1 mm Hg)  2

The following examples are intended to illustrate the present invention and are not intended to limit the reasonable scope thereof.

EXAMPLES

Experimental

Proton and carbon nuclear magnetic resonance (NMR) spectra were recorded on a Varian Gemini 300 NMR instrument operating at 300 MHz in proton mode and 75 MHz in carbon mode. Spectra were plotted using Varian version 6.3A software. All spectra are referenced to TMS at 0 ppm unless otherwise noted. For the proton NMR spectra of acetoacetates, the ratio of the acetoacetate methyl peak(s) at ca. 2.2 to 2.3 ppm to the methyl peak(s) at ca. 1.9 to 2 ppm (enolic methyl) has been found to provide a sensitive measurement for the percent enol content in solutions of acetoacetates. Unless otherwise noted, where percent enol composition is indicated, the tube containing the solution of acetoacetate in the indicated solvent has been allowed to equilibrate at room temperature for a minimum of 24 hours. For proton spectra, a pulse delay of 10 seconds was utilized to assure accurate integration. Proton NMR spectra were typically run at a concentration of 5 to 50 mg experimental compound per gram of solution. Proton and carbon coupling constants were measured directly from line spacings. Thus, in the proton NMR for ABX spin systems the reported $J_{ax}$ and $J_{bx}$ may be slightly in error when $V_a-V_b/J_{ab}$ approaches 2. Carbon NMR spectra were typically run at a concentration of 50 mg per gram of solution. Reported chemical shifts were obtained from fully proton decoupled spectra. For the carbon spectra of single isomers (not mixtures of diastereomers) both multiplicities and carbon-proton coupling constants are reported and were obtained by turning the decoupler off prior to data acquisition. Multiplicities for large one bond couplings (>100 Hz) are reported in capital letters while multiplicities for small long range couplings are reported in lower case letters. Coupling constants are reported as measured. The accuracy of reported coupling constants is assumed to be no less than three times the digital resolution. The linewidth of TMS at half height (resolution enhanced) is reported for all cases in which the line width exceeded six times the digital resolution.

Infrared spectra were recorded on an Nicolet 5DX Spectrophotometer and major peak minima are reported in reciprocal centimeters (cm −1). This instrument is capable of typical resolutions of less than 4 reciprocal centimeters. Infrared spectra were recorded from films (for oils) or KBr pellets for crystalline materials.

Mass spectra (MS) were obtained using a VG Analytical Ltd. Model ZAB-1F Mass Spectrometer in EI (electron impact), fast atom bombardment (FAB, Xenon gas) or FD (field desorption) mode. Gas chromatography-mass spectroscopy (GCMS) and accurate mass measurements (exact mass) were conducted using a VG 70-SEQ instrument equipped with a 30 meter DB5 capillary column (J and W Scientific) using helium carrier gas.

Trace metal analyses were performed by Atomic Absorption (Na) or by ICP (inductively coupled plasma for Fe, Al or Ni) on a Perkin Elmer ICP/6000 instrument. Elemental Analyses (C,H,N) were performed on a Carlo Erba Model 1106 Elemental Analyzer.

Example 1

Preparation of Solketal-acetoacetate

A solution of solketal (1.32 kg, 10 mole) and triethylamine (1.01 g, 0.01 mole) was heated to 60° C. Diketene (840 g, 10 mole) was then added to the resulting solution at a rate such that the temperature of the reaction was maintained between 60° and 80° C. A preliminary rapid distillation of the resulting product was carried out at 0.6 mm Hg and approximately 115° C. A second careful distillation was carried out through a 5 plate Oldershaw column at 0.5 mm Hg. There was thus obtained a colorless liquid which analyzed at 92% solketal-acetoacetate by gas chromatography. Also indicated by gc was 2% dehydroacetic acid and 4.5% solketal. This distilled material was used without any further purification.

$^1$H NMR (CDCl$_3$, digital resolution=0.074 Hz): (keto/enol ratio 91/9) keto form: 4.34 (m, 1H), 4.24 (dd, J=11.4, 4.6, 1H), 4.16 (dd, J=11.4, 6.1, 1H), 4.09 (dd, J=8.5, 6.5, 1H), 3.76 (dd, J=8.5, 6.0, 1H), 3.52 (q, J=0.4, 2H), 2.28 (t, J=0.4, 3H), 1.43 (q, J=0.7, 3H), 1.37 (q, J=0.7, 3H).

Enolic acetoacetyl resonances were observed at 11.9 (OH, bs), 5.05 (CH, q, J=0.7), and 1.97 (CH$_3$, apparent t (believed to be add with equal J), J=0.7).

$^{13}$C NMR (CDCl$_3$, digital resolution=0.512 Hz): 200.3 (Sm), 166.9 (Sm), 109.9 (Sm), 73.3 (Dtt, J=149, 2, 2), 66.2 (Tm, J=149), 65.5 (T and apparent t, J=149, ca. 4), 49.8 (Tq, J=130, 2), 30.2 (Q, J=128) 26.7 (Qq, J=127, 3), 25.3 (Qq, J=126, 3).

MS (Ammonia in methane/chemical ionization): M+1=217

Example 2

Preparation of Solketal-3-hydroxybutyrate

A Zipperclave Autoclave (Autoclave Engineers) was charged with ethylacetate (2.4 L), solketal acetoacetate from Example 1 (609.5 g, 2.82 mole) and Raney Nickel (25 g, W-2 grade, PM-77, water wet) under an inert atmosphere of nitrogen. The nitrogen was displaced with hydrogen to a pressure of approximately 1100 psi. The reaction mixture was then heated with vigorous stirring (1500 rpm) at 60° C. for approximately seven hours. A small (ca. 5 ml) sample of the reaction mixture was removed from the reactor, filtered through celite and concentrated in vacuo. Proton NMR analysis revealed that roughly 2 mole % of unreduced acetoacetate remained. The crude reaction mixture was then heated at 60° C. and 1000 psi hydrogen with vigorous stirring for an additional 5 hours. The autoclave was cooled to room temperature and the hydrogen atmosphere was displaced with nitrogen. The crude reaction mixture was filtered through celite. The resulting solution was extracted in a separatory funnel with saturated aqueous sodium chloride. The organic phase was isolated, filtered through magnesium sulfate and sodium sulfate. The resulting filtrate was concentrated in vacuo to provide an oil (565.11 g, 2.59 mole, approximately 92%). This oil was not purified further but was shown by NMR to be of high purity. Small amounts, <15 total mole %, of ethyl acetate and acetone were also detected.

$^1$H NMR (CDCl$_3$, digital resolution=0.05 Hz): 4.39–4.30 (m, 1H), 4.26–4.17 (m, 1H), 4.26–4.1 (m, 2H), 4.09 (dd, J=8.5, 6.5, 1H), 3.764 (dd, J=8.5, 5.9, 0.5 H), 3.762 (dd, J=8.6,5.8, 0.5H), 3.2–3.0 (bs, 1H=OH), 2.56 (dd, J=16.3, 3.8, 0.5H), 2.55 (dd, J=16.4, 4.2, 0.5H), 2.48 (dd, J=16.3, 8.3, 0.5H), 2.47 (dd, J=16.4, 8.5, 0.5H), 1.44 (m, J=0.7, 3H), 1.37 (q, J=0.6, 3H), 1.239 (d, J=6.3, 1.5H), 1.237 (d, J=6.3, 1.5H).

$^{13}$C NMR (CDCl3, digital resolution=0.191 Hz): 172.5, 172.4; 109.94, 109.92; 73.5, 73.4; 66.17, 66.15; 64.9, 64.8; 64.3, 64.2; 42.93, 42.90; 26.7; 25.29, 25.27; 22.52, 22.49.

IR: 3470 (br), 2985, 2937, 2892, 1739, 1456, 1381, 1373, 1288, 1255, 1216, 1175, 1082, 1058, 1006, 841
Positive FAB: M+1=219
Exact mass (ei): Theory for C$_{10}$H$_{18}$O$_5$—CH3: 203.0919
: Found: 203.0949

Example 3

Preparation of DL-1-(β-hydroxybutyryl) Glycerol

A 500 g solution of solketal acetoacetate was reduced as above in Example 2 in two liters of ethyl acetate. After filtration through celite, the ethyl acetate solution was directly hydrolyzed without further purification. Water (1 L) and Amberlyst 15 ion exchange resin (H+ form, water washed) were added to the ethyl acetate solution containing solketal-3-hydroxybutyrate and the reaction was left to stir overnight. The Amberlyst resin was removed by filtration and the ethyl acetate layer was extracted with water. The brown colored product layer (aqueous phase) and the other water washings were combined, and then heated with activated carbon for 30 minutes on a steam bath. The carbon was removed by filtration through Celite and a light yellow solution of the product was obtained. The water was removed on a rotary evaporator and DL-1-(β-hydroxybutyryl)glycerol (Compound 1, 334 g) was isolated as a light yellow oil.

The above reaction was repeated to provide a total of 508 g of DL-1-(β-hydroxybutyryl)glycerol for evaluation as a parenteral nutrient.

$^1$H NMR (CDCl$_3$, digital resolution=0.079 Hz, TMS at half height=0.51 Hz): 4.24 (m, 3H), 3.95 (m, 1H), 3.71 (dd, J=11.6, 4.0, 1H), 3.620 (dd, J=11.6, 5.8, 0.5H), 3.618 (dd, J=11.6, 5.8, 0.5H), 3.03 (bs, 3OH), 2.56 (dd, J=16.0, 3.8, 1H), 2.47 (dd, J=16.0, 8.8, 1H), 1.26 (d, J=6.3, 3H).

$^1$H NMR (DMSO-d6+10% D20, digital resolution=0.072 Hz): 4.07 (dd, J=11.2, 4.2, 0.5H), 4.06 (dd, J=11.2, 4.2, 0.5H), 4.04 (m, 1H), 3.93 (dd, J=11.2, 6.5, 0.5H), 3.92 (dd, J=11.2, 6.4, 0.5H), 3.67 (m, 1H), 3.37 (m, 2H), 2.39 (2 lines observed, 6.6 Hz separation, 2H), 1.12 (d, J=6.3, 3H).

The pentet (not reported in tabulation for the major isomer) in the proton NMR centered at 4.75 (DMSO-d6) or 5.0 ppm (CDCl$_3$) is taken as evidence for the presence of the secondary ester (2-(3-hydroxybutyryl)-glycerol) at 9–12 mole %. This resonance is assigned to the methine proton of the glycerol nucleus in the secondary ester.

$^{13}$C NMR (CDCl$_3$ (10mg/mL), digital resolution=0.510 Hz): 173.0; 70.08, 70.07; 65.58, 65.56; 64.72, 64.70; 63.40, 63.38; 43.26, 43.23; 22.75, 22.73.

$^{13}$C NMR (DMSO-d6, digital resolution=0.144 Hz, referenced to DMSO at 39.5 ppm): 171.2, 170.9; 69.31, 69.30; 65.5; 63.43, 63.41; 62.7; 44.1; 23.38, 23.37.

IR: 3400 (br), 2975, 2940, 2890, 1725, 1460, 1380, 1296, 1181, 1122, 1063
FDMS: M+1=179
Metal Analysis: Na, 58 ppm; Ni<1 ppm; Fe<4 ppm; Al, 13 ppm
Karl Fischer: Water=2%

| Exact Mass(ci): | Theory for C$_7$H$_{14}$O$_5$ + NH$_4^+$: | 196.1185 |
|---|---|---|
| | Found: | 196.1191 |

Example 4

Evaluation of 1-(DL-β-hydroxybutyryl) Glycerol as Parenteral Nutrient

The molecular weight of the DL-1-(β-hydroxybutyryl) glycerol, Compound 1, from Example 3 is 178 and its estimated energy density is 4.7 kcal/g. Energy density was estimated from literature values for molar heats of combustion of appropriate components in the compound. Heats of combustion are not necessarily equivalent to metabolic energy. The aim of this trial was to determine the response by rats when this monoglyceride was intravenously infused at a rate to provide 50% of the rats estimated daily energy needs while the rat was allowed to orally ingest adequate protein and other nutrients plus half of the estimated dietary energy.

Protocol

Thirty-four male Sprague-Dawley rats with body weights 125 to 150 g were purchased from Harlan Sprague-Dawley, Indianapolis, Ind. and kept at least 3 days prior to beginning any form of pretreatment or treatment. Rats were located in a limited access area which was air conditioned and had controlled 12 hour light-dark cycles. Water was available ad libitum at all times. Rats were housed 4 per cage until pretreatment when they were transferred to individual metabolic cages in which the rat lived throughout the remainder of the experimental period. Pretreatment consisted of inducing general anesthesia with ketamine hydrochloride (10 mg/100 g body weight) and sewing a light weight plastic button on to the nape of the rats neck. The rats were placed in individual metabolic cages adapted to permit continuous intravenous infusion. Rats were allowed 7 days to recover from the stress of having the back button attached, and each rat was monitored for body weight changes and food intake. Any rat which did not exhibit satisfactory growth during this 7 day pretreatment was excluded from testing. Rat diet consisted of solid rat chow for 4 days and complete oral liquid diet (rat diet #711C from Bioserve Inc., Frenchtown, N.J.) for 3 days.

On day 7, each rat was again given general anesthesia as above and surgically prepared for continuous intravenous infusion by placing a silastic catheter in the right external jugular vein. The outer skin was prepped by cleaning with alcohol (ethanol) and betadine solution. A small incision was made in the neck to externalize the superficial jugular vein. The vein was ligated proximally to an opening cut into the vessel, and the silastic catheter threaded into the superior vena cava. The vein was then ligated dorsally to the catheter. The catheter was threaded subcutaneously to the back of the neck where it exited the skin into a wire catheter protector which was anchored to the back button and to a swivel mounted above the cage. Neck skin was closed with staples, and rats were returned to their individual cages. Rats were allowed a minimum of 3 days to recover from surgery. Catheters were kept open by infusing 0.9% saline at 25 mL/day, and rats were fed the liquid oral diet ad libitum. Body weights were measured daily. Any rats which did not exhibit satisfactory recovery were excluded from further treatments.

On day zero, rats were divided into 3 weight matched groups which were distinguished by receiving one of three solutions. Experimental compound was prepared by dissolving 12 grams in 100 mL total volume of 0.9% saline and passed through a 22 micron filter for sterilization. This solution contained 54 kcal/100 mL and was infused at 50 mL/day to provide 27 kcal/day which is 50% of the rats estimated energy requirement. The second group was infused with a 16% glucose solution which provided isocaloric intake. Group three was infused with 50 mL/day with 0.9% saline solution. All rats were switched to a low energy liquid diet which contained similar amounts of protein, vitamins, electrolytes, and minerals but only 50% of the non-protein energy. Rats infused with experimental compound were fed the low energy diet ad libitum. Glucose and saline infused rats had their low energy diet and infusion started 24 hours later than the experimental infused rats because their volume of oral food offered was based on the volume of oral food consumed the previous day by the experimental infused rats. Thus, glucose and saline infused rats were fed the same volume of oral food as that eaten by their matched rats in the experimental group. Day 1 in the results for the glucose and saline infused rats was occurring on the same date as day 2 in the results for the experimental compound infused rats.

Infusate volume, oral food intake, body weight and urinary volume and total nitrogen were monitored daily for each rat. Infusate volume and food intake were determined by weighing the appropriate container at the start and end of each 24 hr period. Measurements were recorded between 9 and 10 AM each day. At the end of the 7th day, rats were sacrificed, and blood and liver were harvested. Plasma was separated for measurement of free fatty acids, glucose, and ketone bodies. Liver was weighed and a sample was fixed in buffered formalin for gross histology.

The data were analyzed for significance by the one-way analysis of variance with repeated measures and comparing the effect of dietary treatment on each day. Tukey's post-hoc test was used to determine which treatments were significantly different. The null hypothesis was concluded invalid if $p \leq 0.05$. The analysis of variance was computed on a SAS statistical package.

For the figures which follow, each point represents the average of all rats in a particular group.

Results

A total of 34 rats were started with intravenous infusion and 5 were lost due to complications from catheters. One rat infused with experimental diet died of causes unknown. The final rat count was 10 rats infused with experimental compound (Compound #1), 8 rats infused with glucose, and 9 rats infused with saline. The final data are averages from these numbers.

Figure 1:
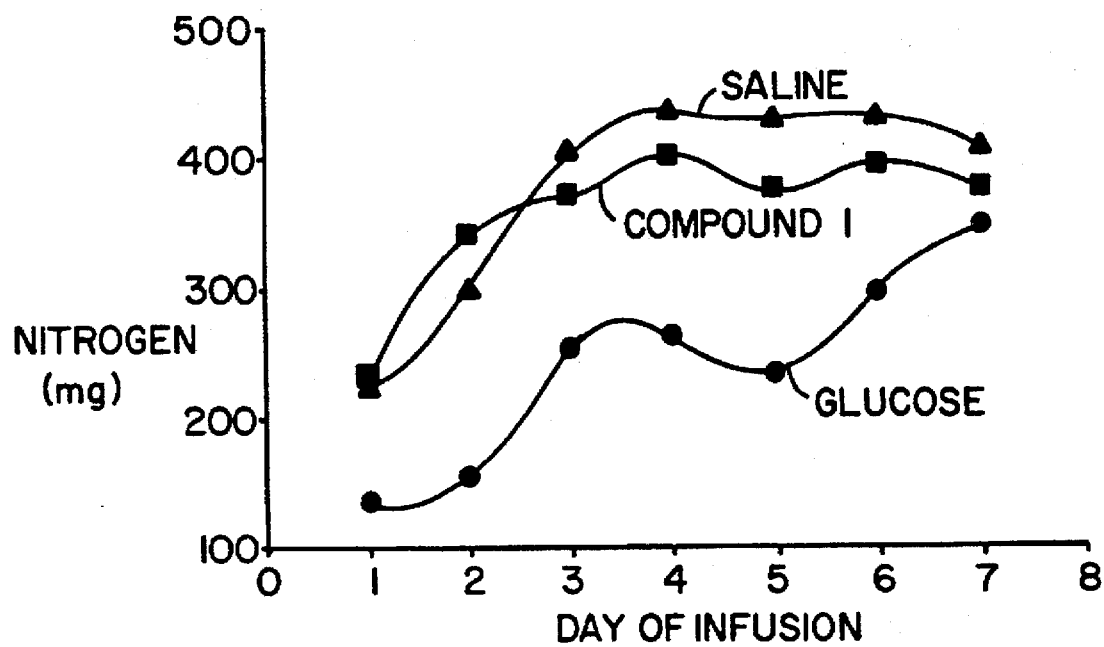
FIG. 1 shows the dietary nitrogen intake in milligrams for three groups of rats that were infused with Compound #1

Dietary nitrogen intake for individual rats is summarized for each group in FIG. 1. All rats were offered similar amounts of oral dietary nitrogen and experimental compound infused rats were fed ad libitum. Other rats were offered similar amounts as the experimental compound infused rats ate.

FIG. 2 illustrates the daily urinary nitrogen losses over 7 days of treatment. The urinary nitrogen loss pattern follows very closely the nitrogen intake pattern illustrated in FIG. 1.

FIG. 3 illustrates the difference between oral intake and urinary nitrogen output which is termed nitrogen balance. It is representative of nitrogen balance because urinary nitrogen is the major route for body loss of nitrogen. Nitrogen balance indicates that the 2 groups of rats receiving energy in their infusions had a tendency to retain more of the dietary nitrogen. Rats receiving saline had a negative nitrogen balance throughout while the other two groups had positive nitrogen balance. The magnitude of positive nitrogen balance is inadequate to support growth. Experience has shown that nitrogen balance must exceed 100 mg/day to show a sustained growth and others have shown that with rats a natural 100 mg/day deficit occurs which cannot be accounted for by nitrogen balance techniques.

FIG. 4 illustrates the change in body weight during the 7 day treatment of the rats. Note that the saline infused rats continually lost weight over 7 days while the other two groups had constant body weights which was consistent with nitrogen balance data.

The liver weight, liver weight per 100 g body weight, and the individual and total ketone body concentrations are shown in Table 1. The liver weights and liver weights per 100 g body weight were similar for rats infused with glucose and the experimental compound while the saline infused rats had significantly smaller livers. Rats infused with saline and experimental compound had similar concentrations of acetoacetate, 3-hydroxybutyrate, and total ketone bodies and all of these values were significantly greater than the values measured for the rats infused with glucose.

1-(DL-β-hydroxybutyryl) glycerol was not acutely toxic and did not show any indication of chronic toxicity. The data indicate that this new monoglyceride was utilized for energy by the rat at least as well as glucose. The data support using a mixture of D(−)-3-hydroxybutyrate and L(+)-3-hydroxybutyrate. However, it is not clear how much of the L(+)-3-hydroxybutyrate is used for energy since it is not likely to be easily metabolized. This monoglyceride of 3-hydroxybutyrate is shown to be a good intravenous nutrient and could be even better if only the D(−)-3-hydroxybutyrate isomer were included.

TABLE I

| RAT NUMBER | WT | LIVER 100/GM | LIVER GLUCOSE | ACAC | BOHB | TKB |
|---|---|---|---|---|---|---|
| SALINE INFUSED RATS | | | | | | |
| 1 | 7.2413 | 3.162139 | 147.5 | 0.109 | 0.356 | 0.465 |
| 2 | 6.4266 | 2.907963 | 133.38 | 0.168 | 0.363 | 0.531 |
| 3 | 6.3369 | 2.975070 | 136.04 | 0.183 | 0.335 | 0.518 |
| 4 | 6.536 | 3.756321 | | 0.167 | 0.2 | 0.367 |
| 5 | 6.6907 | 3.069128 | | | | |
| 6 | 5.7414 | 2.974818 | 138.46 | 0.333 | 0.44 | 0.773 |
| 7 | 5.0192 | 3.280522 | | 0.116 | 0.171 | 0.287 |
| 8 | 3.6041 | 2.120058 | 90.17 | 0.063 | 0.083 | 0.146 |
| 9 | 7.0308 | 3.255 | 139 | 0.316 | 0.318 | 0.634 |
| 10 | 6.0634 | 3.174554 | 129.02 | 0.391 | 0.224 | 0.615 |
| Average | 6.069 | 3.068 | | 0.205 | 0.277 | 0.482 |
| S.E.M.* | 0.340 | 0.130 | | 0.038 | 0.038 | 0.064 |

TABLE I-continued

| RAT NUMBER | WT | LIVER 100/GM | LIVER GLUCOSE | ACAC | BOHB | TKB |
|---|---|---|---|---|---|---|
| EXPERIMENTAL INFUSED RATS ||||||||
| 11 | | | | | | |
| 12 | 9.7384 | 4.234086 | 0.075 | 0.234 | 0.309 | |
| 13 | 8.7184 | 4.403232 | 0.082 | 0.156 | 0.238 | |
| 14 | 10.5651 | 4.110933 | 0.187 | 0.198 | 0.385 | |
| 15 | 10.332 | 5.114851 | 0.227 | 0.553 | 0.78 | |
| 16 | 10.4314 | 4.943791 | 0.181 | 0.399 | 0.58 | |
| 17 | 10.7644 | 4.639827 | 0.154 | 0.248 | 0.402 | |
| 18 | 7.9827 | 4.314972 | 0.113 | 0.593 | 0.706 | |
| 19 | 10.2875 | 4.852594 | 0.358 | 0.446 | 0.804 | |
| 20 | 8.9346 | 4.316231 | 0.264 | 0.558 | 0.822 | |
| Average | 9.751 | 4.548 | 0.182 | 0.376 | 0.558 | |
| S.E.M.* | 0.326 | 0.118 | 0.030 | 0.057 | 0.076 | |
| GLUCOSE INFUSED RATS ||||||||
| 21 | 8.8799 | 3.794829 | 132.68 | 0.078 | | 0.078 |
| 22 | 6.2929 | 2.724199 | 129.17 | 0.197 | 0.371 | 0.568 |
| 23 | 11.3415 | 4.745397 | | | | |
| 24 | 9.2089 | 4.722512 | 86.74 | 0.034 | | 0.034 |
| 25 | 11.4349 | 5.924818 | 96.26 | 0.021 | 0.137 | 0.158 |
| 26 | 12.0103 | 6.159128 | | 0.049 | 0.129 | 0.178 |
| 27 | 6.1504 | 3.727515 | 128.63 | 0.1 | 0.0168 | 0.1168 |
| 28 | 8.1026 | 4.133979 | | 0.065 | 0.169 | 0.234 |
| Average | 9.178 | 4.492 | | 0.078 | 0.165 | 0.195 |
| S.E.M.* | 0.808 | 0.407 | | 0.022 | 0.058 | 0.067 |

*Standard Error of the Mean

Example 5

Preparation of Glycerol-trisacetoacetate

A solution of distilled t-butylacetoacetate (3251.3 g, 20.55 mole) and glycerin (563 g, 6.11 mole) in toluene (250 mL) was heated with distillative removal of the generated t-butanol through a 5 plate Oldershaw column. The initially heterogeneous reaction mixture became homogeneous upon reaching reflux temperature (115°–120° C. internal temperature). After one and then two hours at reflux, additional toluene was added (ca. 1 L each). Distillate was removed at a rate such that the head temperature of the distillate was maintained at or below 100° C. The pot temperature was maintained around 120° C. After a total of 7 hours of heating an additional charge of t-butylacetoacetate (289 g, 1.9 mole) and toluene (800 mL) was added to the reactor. The reaction was allowed to cool to room temperature overnight and heating of the reaction was resumed on the following day. Heating of the reaction mixture was then continued for a total heating time of 14 hours. During the final 30 minutes of heating, the reaction temperature rose from approximately 120° C. to approximately 145° C. The crude reaction product (2064.3 g, 6.00 mole, ca. 98%) was isolated as the undistilled fraction by passing the reaction product through a wiped-film evaporator (Pope Scientific) at 0.5–1 mm/Hg and a wall temperature of 210° C. This process removed volatile materials including t-butylacetoacetate. A portion (1127 g) of this crude product was distilled over a 2 hour period upon passing it through a wiped film evaporator at 0.1–0.05 mm/Hg and a wall temperature of 260° C. The distilled material (923.4 g) was lightly yellow colored. Minimal evidence for decomposition during distillation was obtained. Both the distillate and recovered undistilled 'pot residue' (183.3 g) provided proton NMR data which were consistent with the single product glycerol-trisacetoacetate. Proton NMR analysis of the distilled Sample of glycerol-trisacetoacetate indicated that it contained less than 3 mole % of glycerol-bisacetoacetate.

$^1$H NMR (CDCl$_3$, digital resolution=0.054 Hz): (keto enol ratio =89/11) keto form: 5.4–5.32 (m, 1H), 4.38 (dd, J=12.1, 4.2, 2H), 4.29 (dd, J=12.1, 6.1, 2H), 3.53 (q, J=0.3, 2H), 3.52 (q, J=0.3, 4H), 2.28–2.26 (m, 9H).

Enolic acetoacetyl resonances were observed at 11.82 (primary enolic OH, apparent d, J=0.7), 11.80 (secondary enolic OH, apparent d, J=0.7), 5.02 (CH, poorly resolved multiplet of both primary and secondary enol isomers), 1.981 (secondary enolic CH$_3$, apparent t, J ca. 0.7-coupling to both OH and CH seen in COSY), 1.978 (primary enolic CH$_3$, apparent t, J ca. 0.7-coupling to both OH and CH seen in COSY).

$^{13}$C NMR (CDCl$_3$, digital resolution=0.229 Hz): all keto form: 200.1 (Sm), 200.0*(Sm), 166.6 (Sm), 166.3*(Sm), 69.5 (Dm, J=150.7), 62.5 (Tm, J=149.8), 49.7*(Tq, J=130.6, 1.4), 49.6 (Tq, J=130.4, 1.5), 30.3 (Qt, J=128.2, 0.6), 30.2* (Qt, J=128.2, 0.6).

minor carbon resonances assigned to enol isomers: 177.0* (S), 176.7 (S), 171.8 (S), 171.4*(S), 89.2*(D), 89.1 (D), 21.34*(Q), 21.30 (Q).

IR: 3005, 2965, 2937, 1747, 1716, 1412, 1361, 1320, 1257, 1174, 1147 Peaks marked with an asterisk (*) are assigned as due to the acetoacetate at the secondary position of the glyceride. These peaks (*) were at roughly one-half the intensity of the peaks due to acetoacetates at the symmetrically equivalent primary positions.

FDMS: M+1=345

| Exact Mass | Theory for C$_{15}$H$_{20}$O$_9$—C$_2$H$_2$O | 302.0996 |
|---|---|---|
| | Found | 302.0993 |

Example 6

Preparation of DL-tris-(β-hydroxybutyryl) Glycerol

A Zipperclave Autoclave (Autoclave Engineers) was charged with ethylacetate (2 L), glycerol-trisacetoacetate from Example 5 (888.68 g, 2.58 mole) and Raney Nickel (25 g, W-2 grade, PM-77, water wet) under an inert atmosphere of nitrogen. The nitrogen was displaced with hydrogen to a pressure of approximately 1000 psi. The reaction mixture was then heated with vigorous stirring (1500 rpm) at 60° C. for approximately eight hours. A small (approximately 5 mL) sample of the reaction mixture was removed from the reactor, filtered through cotton and concentrated in vacuo. Proton NMR analysis revealed an approximate 66% decrease in acetoacetyl resonances. Additional Raney Ni catalyst was added (under a nitrogen atmosphere) to the reaction mixture. The reactor was charged with hydrogen as above to 1000 psi and was heated with vigorous stirring at 60° C. for an additional 8 hours. The entire reaction mixture was filtered through celite and concentrated in vacuo to an oil (854.6 g, 2.44 moles, 95%) which was shown to contain less than 1 mole % of ethyl acetate by proton NMR. A careful collection and inspection of the proton NMR revealed 3% of the original acetoacetyl content remained (97% reduction).

Attempts to dissolve this material (845.6 g) in distilled water resulted in an off-white to light yellow cloudy solution. This aqueous solution was stirred with activated carbon (105.2 g) overnight and then filtered through celite. The now clear, light yellow aqueous solution was placed on a freeze-dryer and brought to constant weight (758.64 g, 90% recovery). Trace metal analysis of this material however indicated 120 ppm Ni, 65 ppm Na, and 137 ppm Al. In an attempt to remove trace metals, this oil (750.2 g) was dissolved in saturated aqueous sodium chloride (800 mL). This aqueous solution was extracted in a separatory funnel with ethyl acetate (800 mL). The organic phase was extracted with an additional portion of saturated aqueous sodium chloride (100 mL). The organic phase was filtered through sodium sulfate and concentrated in vacuo to a colorless oil (638.84 g; metals=Ni<1 ppm, 2.4 ppm Fe, 102 ppm Al, and 883 ppm Na). A second extraction of the combined aqueous sodium chloride phases provided an additional batch of DL-tris-betahydroxybutyryl glycerol (61.78 g, 93% combined weight recovery). The material isolated from the first aqueous washing (618.25 g) was dissolved in distilled water (1.2 L) and passed through a glass column (75 mm od×24 in.) containing water washed Bio-Rad AG 501-XS(D) mixed bed ion-exchange resin (882 g). The column was washed with an additional 1000 mL of distilled water. The resulting eluate was collected and brought to constant weight on a freeze-dryer to provide Compound 2 as a clear oil (518.9 g, 84% recovery).

$^1$H NMR (CDCl$_3$): 5.35 (m, 1H), 4.38 (m, 2H), 4.25 (m, 5H), 2.95 (bs, 3 OH), 2.5 (m, 6H), 1.25 (m, 9H)

$^{13}$C NMR (CDCl$_3$, digital resolution=0.573 Hz; referenced to CDCl3 at 77.1 ppm): 172.12, 172.10 (2C); 171.74, 171.72 (1C); 69.01, 68.97, 68.96, 68.92 (1C), 64.0 (3C); 62.0 (2C); 43.1, 42.9, 42.8 (3C), 22.4 (3C) IR: 3400 (br), 2980, 2940, 1736, 1460, 1410, 1380, 1293, 1255, 1176, 1125, 1080, 950, 857.

Metal Analysis: Na, 2 ppm; Ni<1 ppm; Fe 1 ppm; Al, 20 ppm.

Karl Fischer: Water=3.73%

Positive FAB: M+1=351

Elemental Analysis:

Calc. for $C_{15}H_{26}O_9$: C, 51.42; H, 7.48

Calc. for $C_{15}H_{26}O_9$:

(with 4.1% water): C, 49.31; H, 7.63

Found: C, 49.29; H, 7.39

Example 7

Evaluation of DL-tris(β-hydroxybutyrl) Glycerol as Parenteral Nutrient

This compound has a molecular weight of 350 and its estimated energy density is 4.72 kcal/g. It was tested for use as a parenteral nutrient in rats as described in Example 4.

Results and Comments

A total of 29 rats were started with intravenously infusion and 4 were lost due to complications. Two glucose infused rats had catheter complications and were terminated, and one glucose and one experimental compound infused rat died for causes unknown. The rat final count was 9 rats infused with experimental compound (Compound #2), 9 rats infused with saline, and 7 rats infused with glucose. The final data are averages from these numbers.

Dietary nitrogen intake for the rats is summarized for each group in FIG. 5. All rats were offered similar amounts of oral dietary nitrogen, and experimental compound infused rats were fed ad libitum. Other rats were offered amounts similar to that which the experimentally fed rats ate. Although rats were pair-fed throughout the infusion period, there is a variation in the nitrogen intake. Dietary nitrogen for rats infused with glucose is complicated by the loss of 3 rats; their data is not included; and by the failure of glucose infused rats to eat all of their food. The nitrogen intake for the saline infused rats was lowered by the refusal of one rat to eat more than 10% of the offered diet. Nonetheless this rat did not lose weight for the first three days of the saline infusion. It's body weight held constant.

Urinary nitrogen losses for individual rats are summarized for each group in FIG. 6. The pattern of urinary nitrogen output Was similar to that for nitrogen intake with rats infused with glucose having the lowest output and rats infused with experimental compound had the highest.

The difference between nitrogen intake and output is summarized for each group in FIG. 7. Note that rats fed the experimental compound always had a nitrogen retention of approximately 100 mg or greater. Nitrogen retention data for the other two groups was not different.

FIG. 8 present the body weight data for the groups. The saline infused rats were clearly losing body weight over the seven day period while the other two groups were essentially maintaining their body weight. These data clearly show that the experimental compound was being utilized for energy.

Table 2 lists the liver weight, liver weight/100 g body weight, plasma free fatty acids, plasma glucose, and plasma ketone bodies. The total and relative liver weights were similar for glucose and experimental compound infused rats, and both treatment groups had larger values than did saline infused rats. Saline infused rats had more free fatty acids in the plasma than did the other two treatment groups. Ketone bodies were highest and glucose lowest for rats infused with the experimental compound. In contrast, ketone bodies were lowest and glucose highest for glucose infused rats.

DL-tris-(β-hydroxybutyryl)glycerol was not acutely toxic and did not induce any indications of chronic toxicity. Infusion of DL-tris-(β-hydroxybutyryl) glycerol did indeed elevate plasma ketone bodies which indicated hydrolysis, and body weight and nitrogen data indicate that the compound was providing energy to the rat. In support of body weight, this compound was as good as glucose. There were no clear differences between glucose and this experimental compound in terms of nitrogen metabolism.

TABLE 2

| GROUPS | LIVER 1 g | LIVER 2 g/100 g bw | FFA micromol | GLUCOSE mmol/dl | KETONES mmol/l |
|---|---|---|---|---|---|
| Saline | 7.1(0.2) | 2.9(0.1) | 435(35) | 136(4) | 0.47(0.06) |
| Glucose | 8.9(0.5) | 3.4(0.1) | 386(30) | 144(5) | 0.20(0.04) |
| Compound #2 | 8.9(0.3) | 3.4(0.1) | 360(24) | 126(5) | 0.82(0.03) |

Compound refers to DL-tris-(β-hydroxybutyryl)glycerol.

We claim:

1. A process for the production of solketal-β-hydroxybutyrate comprising:

(a) reacting at a temperature of about 0° to 180° C. solketal and an acetoacetate compound selected from the group consisting of acetoacetate ester and acetoacetate precursor to produce an intermediate solketal acetoacetate derivative, and (b) reducing said intermediate solketal acetoacetate derivative in the presence of hydrogen and a hydrogenation catalyst at a temperature of about 25° to 140° C.

2. The process according to claim 1 wherein said solketal-β-hydroxybutyrate is further treated by hydrolyzing in the presence of an acid catalyst at a temperature from about 0° to 60° C. to remove the protecting groups.

3. The process according to claim 2 wherein said solketal is treated in step (a) with diketene in the presence of a basic catalyst.

4. The process according to claim 3 wherein said basic catalyst is a tertiary amine.

5. The process according to claim 4 wherein said tertiary amine is selected from the group consisting of trimethylamine, triethylamine, tripropylamine, pyridine, dimethylaminopyridine and mixtures thereof.

* * * * *